United States Patent [19]
Knapp

[11] Patent Number: 4,746,213
[45] Date of Patent: May 24, 1988

[54] PROCESS AND DEVICE FOR TESTING LIQUID MEDICAMENTS

[76] Inventor: Dieter Knapp, Fahrenbacher Str. 22, D-6149 Fürth/Odw., Fed. Rep. of Germany

[21] Appl. No.: 866,609

[22] PCT Filed: Sep. 4, 1985

[86] PCT No.: PCT/EP85/00444
§ 371 Date: May 16, 1986
§ 102(e) Date: May 16, 1986

[87] PCT Pub. No.: WO86/01892
PCT Pub. Date: Mar. 27, 1986

[30] Foreign Application Priority Data
Sep. 18, 1984 [DE] Fed. Rep. of Germany ....... 3434154

[51] Int. Cl.⁴ .................. G01N 21/68; G01N 21/69; G03B 41/00
[52] U.S. Cl. ........................ 356/311; 354/3; 354/354
[58] Field of Search .......... 356/311, 313, 314; 354/354, 3

[56] References Cited
U.S. PATENT DOCUMENTS
2,920,201 1/1960 Annis et al. ............ 356/313
4,195,641 4/1980 Joines et al. ............ 356/311

OTHER PUBLICATIONS
Elektor, vol. 3, No. 10, Oct. 1977, "Kirlian Photography", pp. 10-05 to 10-08.
Boyers et al., "Corona Discharge Photography", Jour. of Applied Physics, vol. 44, No. 7, Jul. 1973, pp. 3102-3112.

Primary Examiner—Vincent P. McGraw
Attorney, Agent, or Firm—Burns, Doane, Swecker & Mathis

[57] ABSTRACT

A liquid drug is tested by creating an electric corona discharge in the vicinity of a generally wedge-shaped layer of the drug, and recording the image thereof on a photographic film. The film is placed on the top side of an insulation plate, and the drug is disposed between the film and a convex end of a displaceable electrode. The wedge-shaped layer of the drug is created by pressing the electrode against the film. A high frequency generator is connected to an electrode disposed on the bottom side of the plate to create the corona discharge.

9 Claims, 1 Drawing Sheet

PROCESS AND DEVICE FOR TESTING LIQUID MEDICAMENTS

BACKGROUND OF THE INVENTION

The invention concerns a process and an apparatus for the testing of liquid drugs, in particular also homeopathic preparations.

Drugs may be tested conventionally by chemical, chromatographic or spectrographic processes and by tests on living organisms. It is also possible to investigate drugs by simple testing with sensory organs with respect to trubidity, olfactory changes or the like.

It is common to all of the conventional processes that they are either highly inaccurate or providing little information. It is therefore necessary in most cases to rely on the fact that a solution of drug remains usable for a certain period of time, if certain storage rules are observed, in particular with respect to temperature and light effects. This period of time within which a drug may be used, must as a precautionary measure be relatively short, in order to maintain an adequate degree of safety. If damage to a drug occurred at an unusually early point in time, for example as the result of unnoticed external effects, or if a drug has undergone changes during or shortly after its preparation, this may be determined only with very expensive investigating methods, which in most cases can be performed in the manufacturing plant only, or not at all.

It is therefore the object of the ivention to provide a process for the testing of liquid drugs that may be carried out in a very simple manner and is applicable to highly different drugs and which makes it possible to clearly detect even slight deviations from comparative samples, so that both in the case of freshly prepared drugs and with drugs that have been stored for longer periods of time, rapid and comprehensive testing is possible, said process being capable of detecting changes which may be ascertained with conventional testing methods at great expense only or not at all.

SUMMARY OF THE INVENTION

This object is attained according to the invention by triggering an electric corona discharge in an approximately wedge-shaped layer of the liquid drug, optically recording the discharge and evaluating it.

It has been discovered surprisingly that in the image of such a corona discharge even slight changes in the drug, for example in relation to the concentration of the solution or an aging process, may be observed very clearly. The process further demonstrates changes which affects the activity of the drug but cannot be detected by other chemical or physical processes without ambiguity, so that biological test methods, such as experiments on animals or cell cultures may be omitted.

It has been found appropriate to conduct the testing process both with respect to the experimental method and the evaluability and comparability of the images obtained, in a manner such that the corona discharge takes place between a convex electrode surface and the surface of a dielectric material. The gap, which is wedge-shaped in its cross-section, extends annularly around the apex of the curved electrode surface.

Optical recording is carried out conveniently by photographic means, but electronic image storage and electronic image scanning are also possible, for example by means of a laser beam.

According to an advantageous embodiment of the invention, the liquid drug is applied to the surface of a photographic layer directly, or with the interposition of a glass object carrier, and a convex electrode is pressed onto the photographic layer or the glass object carrier with a predetermined force. By this method in the photographic layer, which may be applied to a photographic film or photographic plate, a particularly sharp image of the corona discharge phenomena may be obtained, especially if the drug is placed onto the photographic layer.

The invention further relates to an apparatus for the carrying out of the process. This apparatus is characterized in that a flat electrode connected with a high frequency generator is placed onto the reverse side of an insulating plate and that a displaceable electrode provided with a convex contact surface may be pressed against a carrier of a photographic layer on the side of the insulating plate facing away from the flat electrode.

This apparatus is of a relatively simple configuration and makes possible rapid testing, so that several smaples may be examined at short intervals.

THE DRAWINGS

The invention will become more apparent from the examples of embodiment described below with reference to the drawing. In the drawing:

FIG. 1 shows in a simplified manner an apparatus equipped with a high frequency generator for the examination of liquid drugs, FIG. 2 in an enlarged representation corresponding to FIG. 1, the convex terminal section of the electrode wetted with the drug and placed onto the photographic layer, and FIG. 3 is a representative similar to FIG. 1 a modified form of embodiment of the apparatus.

DETAILED DESCRIPTION OF THE PREFERRED EMBODIMENTS OF THE INVENTION

Figure 1:
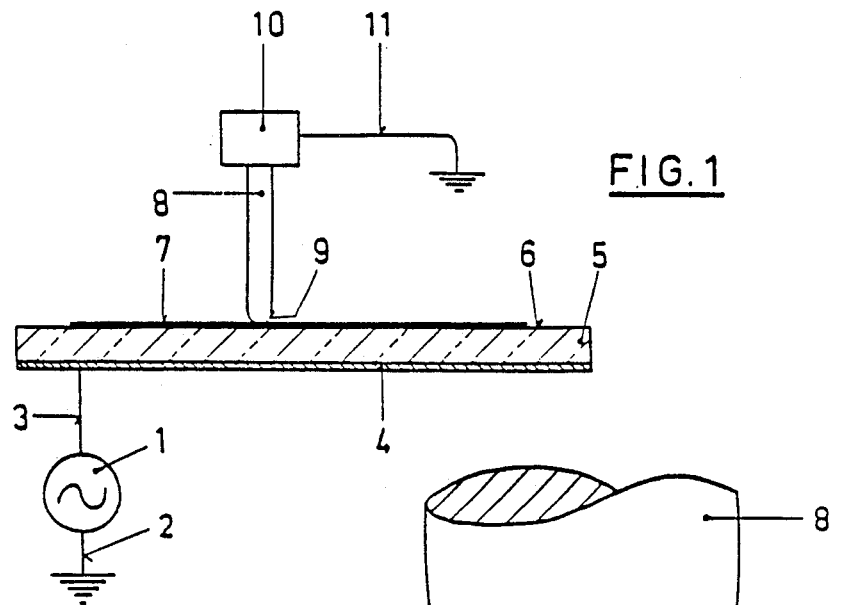
Figure 2:
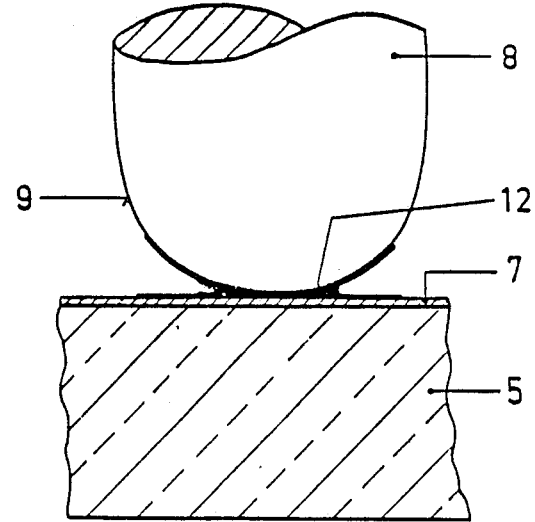

The test apparatus shown in FIG. 1 comprises a high frequency generator 1, one terminal 2 of which is grounded and the other terminal 3 is connected with a flat electrode 4, applied against the bottom side of a glass plate 5. The flat electrode 4 may consist for example of a vapor deposited metal layer.

A photographic film 7 is placed on the top side 6 of the glass plate 5 for each test, to serve as the carrier of the photographic layer. Testing is performed in a dark room.

A displaceable electrode 8, for example a metallic rod made of brass or another material having good conductivity, is cylindrical in shape and is provided with a convex electrode surface 9 at its lower end, which in the present example consists of a hemispherical surface with the radius of the cylindrical electrode 8.

The electrode 8 carries at its upper end a weight 10, whereby the contact pressure of the convex electrode surface 9 on the photographic film 7 is determined. The electrode 8 is grounded by means of a line 11 (FIG. 1).

A sample 12 of the liquid drug to be examined is introduced into the zone between the convex surface 9 and the film 7. As the electrode 8 is in contact with its apex with the surface of the film 7, the sample fills an essentially wedge-shaped annular space and wets the convex electrode surface 9 and the surface of the film 7. The liquid sample 12 to be examined may be applied in a very simple manner by at first immersing the electrode 8 in a vessel containing the liquid drug to be investigated. The drug wets the immersed part of the electrode 8 and also contacts the surface of the film 7, when the convex electrode surface is pressed onto the film 7. Alternatively, the liquid sample to be examined may initially be placed onto the surface of the film 7 prior to the placing of the electrode 8. It is obvious that the electrode surface 9 must be carefully cleaned prior to the experiment, for example by rubbing with alcohol.

Figure 3:
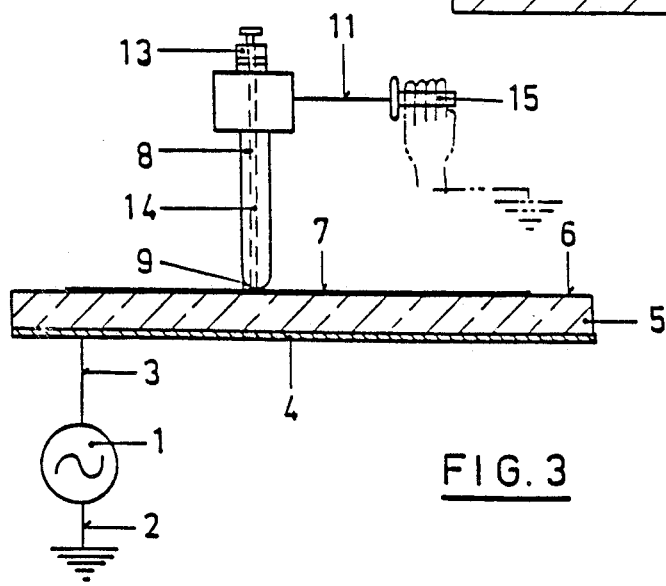

It is further possible to equip the electrode 8 itself with a metering device 13—merely indicated in FIG. 3—whereby a predetermined volume of the liquid drug to be examined may be introduced into the zone between the contact surface 9 and the film 7 through a center feeder bore 14 opening into the convex contact surface 9.

By means of the high frequency generator 1, which is operated for example with a cycle frequency of 1 Hz to 10 kHz and which generates a voltage of 5-50 kV, an electric corona discharge is produced in the area around the contact point between the electrode 8 and the film 7 and recorded on the film 7. Only those drug samples which are identical in their composition and their chemical and biological effects, yield identical discharge images. Clearly recognizable deviations in the discharge images indicate changes in the substance investigated. For example, changes due to aging may be detected, which cannot be determined with other testing methods, or only at great expense and with reduced reliability.

In contrast to the example of embodiment according to FIG. 1, wherein the electrode 8 is grounded directly by means of the line 11. In the example according to FIG. 3 the line 11 connected with the electrode 8 is further electrically connected with a manual handle 15. If a person is holding the handle 15, the electrode 8 is grounded through this person. The discharge images produced by this layout permit certain conclusions concerning the individual effectiveness of the drug being examined.

In a deviation from the examples of embodiment described above, the liquid sample 12 to be examined may also be applied to a glass object holder resting on the film 7. It has been found, however, that the sharpest and thus the most informative images are obtained by placing the sample 12 directly onto the surface of the film 7.

What is claimed is:

1. Process for the testing of liquid drugs characterized in that in a thin, approximately wedge shaped layer of the liquid drug an electric corona discharge is triggered, the image whereof is optically recorded and evaluated.

2. Process according to claim 1, characterized in that the corona discharge takes place between a convex electrode surface and the surface of a dielectric material.

3. Process according to claim 1, characterized in that the optical recording is effected by photographic means.

4. Process according to claim 3, characterized in that the liquid drug is applied to the surface of a photographic layer directly or with the interposition of a glass object holder and that a convex electrode is pressed onto the photographic layer or the glass object with a predetermined force.

5. Apparatus for testing liquid drugs, comprising:
   an insulating plate carrying a first electrode on one side thereof,
   a second electrode having a convex contact surface arranged to face a second side of said plate which is opposite said first side,
   a photographic film arranged on said second side so as to be disposed between said contact surface and said second side,
   means producing relative movement between said plate and said contact surface to bring said plate and contact surface together such that a layer of a liquid drug positioned between said contact surface and said photographic film is caused to assume an approximate wedge shape, and
   a high frequency generator connected to said first electrode for creating an electric corona discharge in the vicinity of the drug sample, the image of which is recorded by said photographic film.

6. Apparatus according to claim 5, wherein said second electrode comprises a cylindrical metal rod, said rod having a hemispherical end which defines said contact surface.

7. Apparatus according to claim 5, wherein said second electrode includes a bore therethrough for conducting a supply of liquid drug being tested.

8. Apparatus according to claim 5, wherein said second electrode is electrically grounded.

9. Apparatus according to claim 7 including a manually supportable handle connectible to said second electrode to ground the latter.

* * * * *